(12) United States Patent
Yamamoto

(10) Patent No.: US 8,534,454 B2
(45) Date of Patent: Sep. 17, 2013

(54) CONVEYOR AND METHOD OF MANUFACTURING ABSORBENT ARTICLE

(75) Inventor: Hiroki Yamamoto, Kanonji (JP)

(73) Assignee: Uni-Charm Corporation, Shikokuchuo-Shi, Ehime (JP)

( * ) Notice: Subject to any disclaimer, the term of this patent is extended or adjusted under 35 U.S.C. 154(b) by 454 days.

(21) Appl. No.: 12/716,019

(22) Filed: Mar. 2, 2010

(65) Prior Publication Data

US 2010/0181007 A1    Jul. 22, 2010

(30) Foreign Application Priority Data

Mar. 2, 2009   (JP) .............................. P 2009-048418
Feb. 26, 2010  (JP) .............................. P2010-042003

(51) Int. Cl.
*B65H 23/02*   (2006.01)
(52) U.S. Cl.
USPC ............. 198/819; 198/394; 198/395; 156/64; 156/378
(58) Field of Classification Search
None
See application file for complete search history.

(56) References Cited

U.S. PATENT DOCUMENTS

| | | | |
|---|---|---|---|
| 1,591,906 A | | 7/1926 | Wood et al. |
| 3,147,898 A | * | 9/1964 | Huck .............................. 226/17 |
| 4,116,399 A | | 9/1978 | Mosburger et al. |
| 4,726,501 A | * | 2/1988 | Wiley .............................. 226/15 |
| 2005/0056678 A1 | * | 3/2005 | Nomura et al. .................. 226/21 |
| 2006/0196594 A1 | | 9/2006 | Shimizu |

FOREIGN PATENT DOCUMENTS

| | | |
|---|---|---|
| DE | 1944633 A1 | 3/1971 |
| DE | 2252490 | 5/1974 |
| GB | 352670 A | 7/1931 |
| JP | 2004-262556 A | 9/2004 |

OTHER PUBLICATIONS

Extended European Search Report dated Aug. 27, 2012 for Application No. 10748873.6.
Office Action in Mexican Application No. MX/A/2010/002485 mailed Nov. 5, 2012.
International Search Report and Written Opinion as issued on Jun. 1, 2010 in counterpart PCT Patent Application.

* cited by examiner

*Primary Examiner* — Kavel Singh
(74) *Attorney, Agent, or Firm* — Lowe Hauptman & Ham, LLP

(57) ABSTRACT

The web conveyor conveys a continuous web for L size or M size. The conveyor includes a guide mechanism changing a passing position of a side edge portion of the web, a detection mechanism detecting the passing position of the edge portion of the web, and a drive mechanism moving the guide mechanism and the detection mechanism together in the cross direction of the web according to the L size or M size, by being in contact with a first side edge portion and a second side edge portion of the web. The drive mechanism moves the guide mechanism and the detection mechanism by an equal traveling distance in the cross direction of the web.

13 Claims, 8 Drawing Sheets

CONVEYOR AND METHOD OF MANUFACTURING ABSORBENT ARTICLE

TECHNICAL FIELD

The present disclosure relates to a conveyor and a method of manufacturing an absorbent article using such a conveyor to selectively convey continuous webs of different sizes.

BACKGROUND ART

A method of manufacturing an absorbent article such as a pants-type diaper, a sanitary napkin and a panty liner is implemented in an assembly line. For instance, a continuous web including a continuum of top sheets and a continuum of back sheets to form absorbent articles is conveyed under tension in a web conveyance direction by a conveyor. Then, component members such as a gather (elastic member) and a waterproof film are placed on the web being conveyed under tension in the web conveyance direction.

In some cases, a side edge portion of a web during conveyance may be misaligned in a cross direction (a web width direction) perpendicular to a web conveyance direction. To address this problem, there is a known conveyor configured to adjust the passing position where a side edge portion of a web passes during conveyance (see PTL 1, for example). Specifically, the conveyor includes nip rollers, an actuator and a sensor as a detection mechanism.

The nip rollers include two rollers configured to hold at least one of side edge portions of a web. The nip rollers are each rotatable about one end of a shaft in a plan view of the web. The actuator is coupled to the nip rollers through an arm and the like, and rotates the nip rollers. The sensor detects the passing position of the side edge portion of the web after passing between the nip rollers.

In the conveyor thus configured, when the sensor determines that the passing position of the side edge portion of the web is misaligned from a predetermined position, the nip rollers are rotated by the actuator to guide the side edge portion of the web outward or inward in the web width direction. Thereby, the conveyor can adjust the passing position of the side edge portion of the web.

Absorbent articles are manufactured in different sizes, such as S size, M size and L size. In this regard, the aforementioned conveyor can convey webs of various sizes by moving the actuator coupled to the nip rollers, and the sensor independently of each other in the web cross direction.

The inventors have discovered that when the size of a web to be being conveyed is changed to a different one, and the actuator and the sensor are independently moved in the web cross direction, and therefore the nip rollers (the actuator) and the sensor may be sometimes misaligned in an inappropriate positional relationship. In this case, the inappropriate positional relationship causes the nip rollers to be rotated by an erroneous amount. To avoid this, the positional relationship between the nip rollers and the sensor needs to be adjusted to a predetermined relationship, which, in turn, requires complicated control for this adjustment. It is desirable to provide a conveyor and a method of manufacturing absorbent articles which are capable of selectively conveying webs of different sizes by changing a passing position of a side edge portion of the web, without having to perform complicated control and/or adjustment.

Under these circumstances, the present invention is aimed to provide a conveyor and a method of manufacturing an absorbent article which are capable of selectively conveying any of webs for two or more sizes by easily changing a passing position of a side edge portion of the web without having to perform complicated control.

CITATION LIST

Patent Literature

PTL 1. Japanese Patent Application Publication No. 2004-262556 (pp. 2 and 3, FIGS. 2 and 3)

SUMMARY

To solve the above-described problem, the present invention has the following aspects. A aspect of the present invention provides a conveyor that conveys selectively one of a continuous web for a first size and a continuous web for a second size, comprising: a guide mechanism configured to change a passing position of at least one of side edge portions of the web by being in contact with the side edge portion of the web; a detection mechanism configured to detect the passing position of the side edge portion of the web; and a drive mechanism configured to move the guide mechanism and the detection mechanism in a cross direction perpendicular to a conveyance direction of the web according to any one of the first size and the second size by an equal traveling distance in the cross direction of the web.

According to the aspect of the present invention, there can be provided a conveyor and a method of manufacturing an absorbent article which are capable of selectively conveying any of webs for two or more sizes by easily changing a passing position of a side edge portion of the web without having to perform complicated control.

DETAILED DESCRIPTION

Hereinafter, a conveyor and a method of manufacturing an absorbent article according to one or more embodiments of the present invention will be described with reference to the accompanying drawings. Note that, in the following description of the drawings, same or similar reference signs denote same or similar elements and portions. In addition, it should be noted that the drawings are schematic and are not to scale unless otherwise specified. Therefore, specific dimensions and the like should be determined in consideration of the following description. Moreover, the drawings do not necessarily reflect the real-life dimensional relationships and ratios of components.

Firstly, a configuration of an absorbent article 1 according to one or more embodiments will be explained with reference to FIG. 1 which is a partially cutaway perspective view showing the absorbent article 1. In this particularly illustrated embodiment, the absorbent article 1 is a disposable pants-type diaper for adults. The absorbent article 1 may have different sizes, such as L size (first size) and M size (second size).

Figure 1:
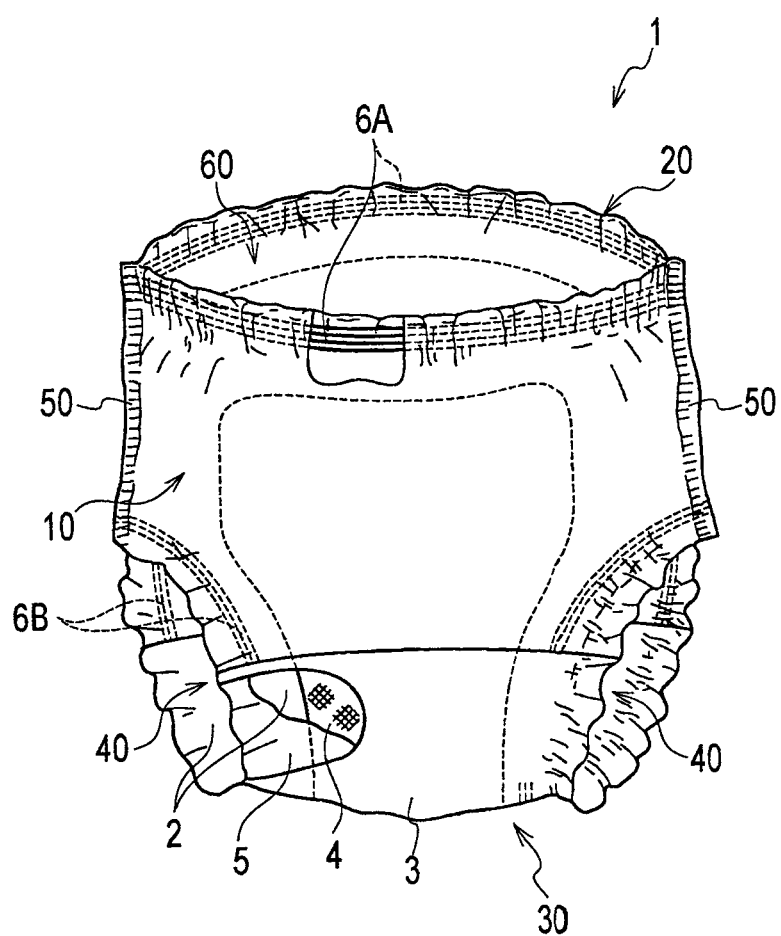
FIG. 1 is a partially cutaway, perspective view of an absorbent article according to one or more embodiments.

As shown in FIG. 1, the absorbent article 1 mainly includes a top sheet 2, a back sheet 3, an absorber 4 and a waterproof sheet 5.

The top sheet 2 is adapted to come into contact with the skin of a person to wear the absorbent article 1 (hereinafter, "wearer"). The top sheet 2 is made of a liquid permeable sheet such as a nonwoven fabric or a perforated plastic film. The back sheet 3 is provided outside the top sheet 2 (on the side facing away from the wearer). The back sheet 3 is made of a nonwoven fabric or the like.

The absorber 4 is provided between the top sheet 2 and the back sheet 3, and for absorbing excretion discharged from the wearer. The absorber 4 is made of a mixture of ground pulp and superabsorbent polymer particles, or the like. The waterproof sheet 5 is provided between the back sheet 3 and the absorber 4, for blocking the permeation of the excretion from the wearer to the outside of the absorbent article 1. The waterproof sheet 5 is made of a liquid impermeable sheet.

The absorbent article 1 thus configured includes, in combination, a front waistline portion 10 to be fitted to the front waist of a wearer, a back waistline portion 20 to be fitted to the back waist of the wearer, and a crotch portion 30 to be fitted to the crotch of the wearer. Incidentally, leg-surrounding openings 40 into which the legs of the wearer are inserted are formed at both sides of the crotch portion 30.

The front waistline portion 10 and the back waistline portion 20 are joined together by joint portions 50, and thereby form a waist opening to be fit around the body of the wearer. A waist gather 6A made of a stretchable rubber strand or the like is provided to an entire peripheral edge of the front waistline portion 10 and the back waistline portion 20.

For example, to make the front waistline portion 10 and the back waistline portion 20 stretchable in the cross direction perpendicular to the front-to-back direction from the front waistline portion 10 toward the back waistline portion 20, the front waistline portion 10 and the back waistline portion 20 may be provided with the waist gather 6A, or may themselves be made of a stretchable sheet.

The crotch portion 30 is provided between the front waistline portion 10 and the back waistline portion 20. Leg gathers 6B made of stretchable rubber strands or the like are provided on both sides of the crotch portion 30.

For example, to make the crotch portion 30 stretchable in the leg-encircling, the crotch portion 30 may be provided with the leg gathers 6B, or may itself be made of a stretchable sheet.

Secondly, a method of manufacturing absorbent articles according to one or more embodiments will be explained with reference to FIG. 2 which is a diagram for explaining a relevant part of the absorbent article manufacturing method.

Figure 2:
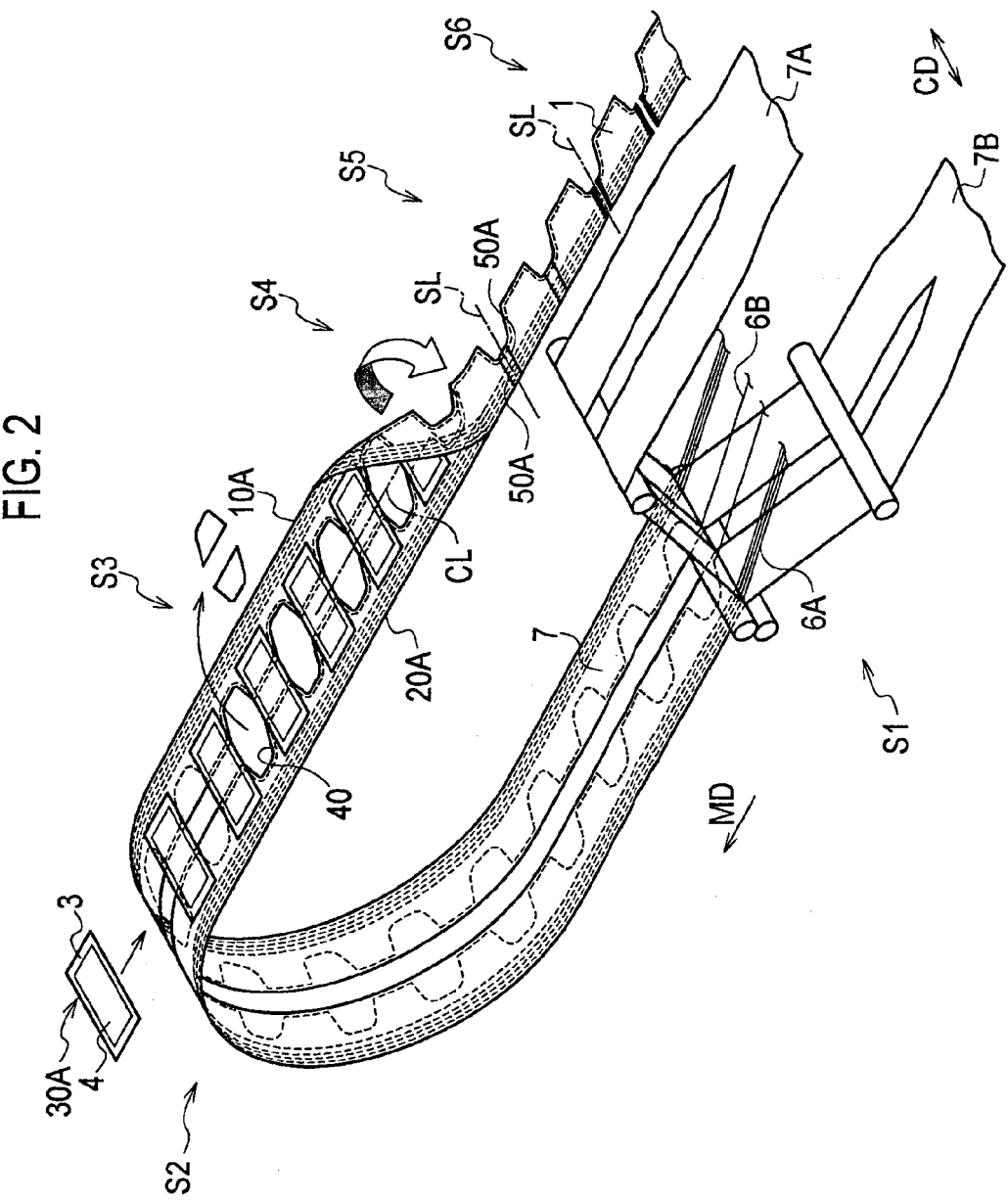
FIG. 2 is a diagram for explaining a relevant part of a method of manufacturing absorbent articles according to one or more embodiments.

As shown in FIG. 2, the method of manufacturing absorbent articles includes at least a waistline forming step S1, an absorber transferring step S2, a leg-surrounding forming step S3, a folding step S4, a joining step S5 and a cutting step S6.

In the waistline forming step S1, gathers (a waist gather 6A and/or a leg gather 6B) are placed between a web 7A and a web 7B, and thereby a web 7 prepared to form the front waistline portion 10 and the back waistline portion 20 is formed.

Note that the web 7 (webs 7A, 7B) during conveyance is stretchable in a cross direction CD (width direction) perpendicular to a conveyance direction MD (machine direction) of the web 7. In addition, the web 7 is asymmetrical with respect to a center line CL that bisects a width in the cross direction CD of the web 7 and extends in the conveyance direction MD of the web 7.

In the absorber transferring step S2, a crotch portion member 30A to form the crotch portion 30 is transferred onto the web 7, more specifically, between the front waistline portion 10 and the back waistline portion 20 after the waistline forming step S1. Here, the crotch portion member 30A includes the back sheet 3 and the absorber 4.

In the leg-surrounding forming step S3, the leg-surrounding openings 40 (so-called leg holes) are formed by cutting the web 7 (webs 7A, 7B) after the absorber transferring step S2. Here, the formation of the leg-surrounding opening 40 does not necessarily involve cutting only the web 7A and the web 7B, but may involve cutting, together with the web 7A and the web 7B, the back sheet 3 constituting the crotch portion member 30A.

Note that the absorber transferring step S2 and the leg-surrounding forming step S3 may be performed in the reverse order.

In the folding step S4, the web 7 is folded into two parts along a folding line extending in the conveyance direction MD of the web 7 by bringing a side edge portion (first side edge portion 10A) of the front waistline portion 10 toward a side edge portion (second side edge portion 20A) of the back waistline portion 20, after the leg-surrounding forming step S3.

Note that, in this particularly illustrated embodiment, the folding line is the center line CL. However, the folding line is not necessarily the center line CL, and may be shifted from the center line CL toward either of the first side edge portion 10A and the second side edge portion 20A.

In the joining step S5, the folded parts of the web 7 are joined together in joint regions 50A through ultrasonic treatment or heat treatment after the folding step S4. The joint region 50A extends in the conveyance direction MD across an imaginary line SL that indicates a to-be-cut position and extends in the cross direction CD of the web 7.

In the cutting step S6, the web 7 joined in the joint regions 50A is cut along the imaginary lines SL after the joining step S5. Thereby, the absorbent article 1 is manufactured.

Here, the method of manufacturing absorbent articles includes conveying steps between the steps (S1 to S6). In each of the conveying steps, the web 7 to be processed into the absorbent article 1 is conveyed by a conveyor 100, which will be described later. This conveying step includes a changing step of changing the passing position of a side edge portion of the continuous web 7 to be processed into the absorbent article 1 during conveyance of the web 7.

Figure 3:
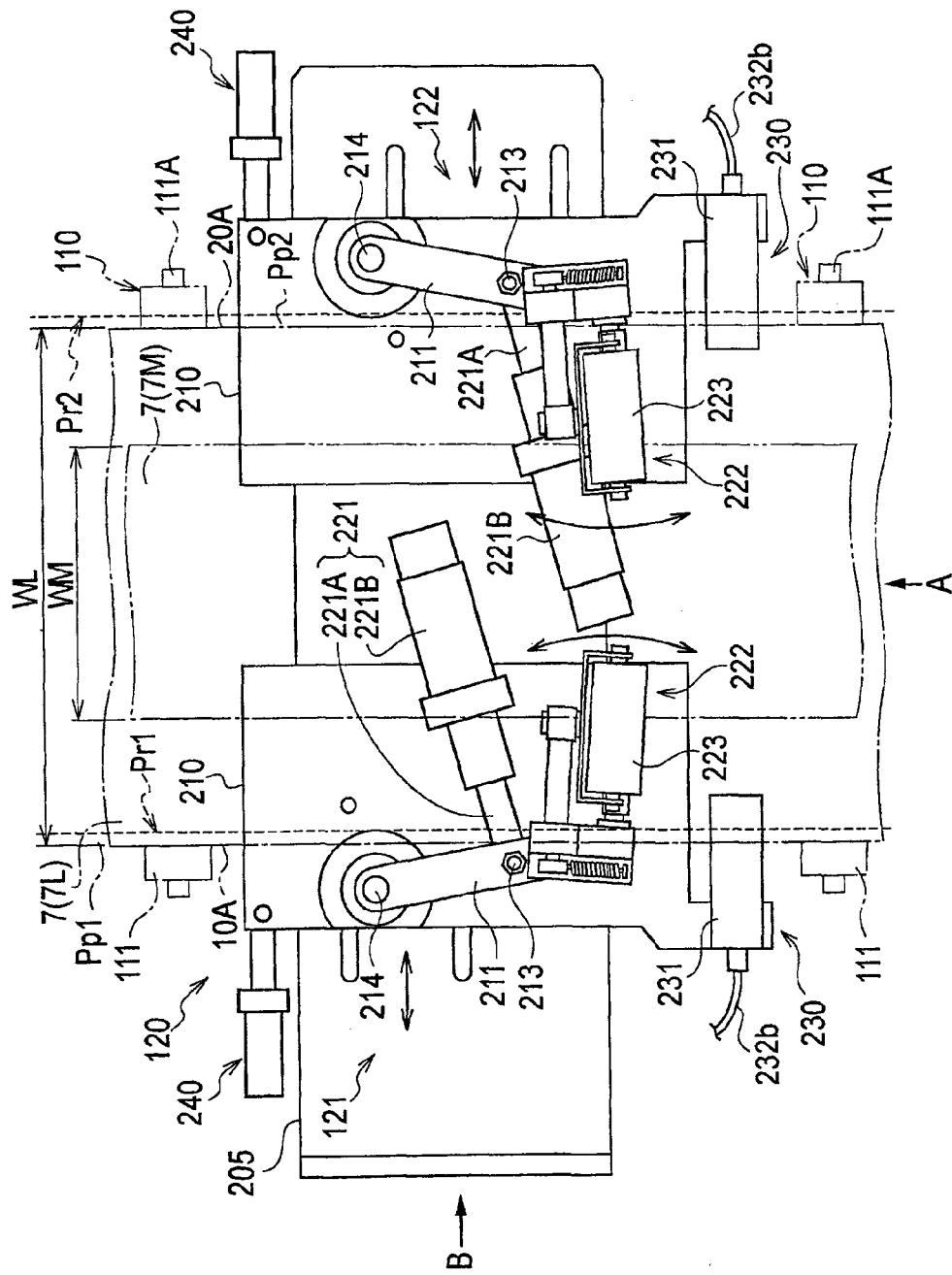
FIG. 3 is a plan view of a conveyor according to one or more embodiments.
Figure 4:
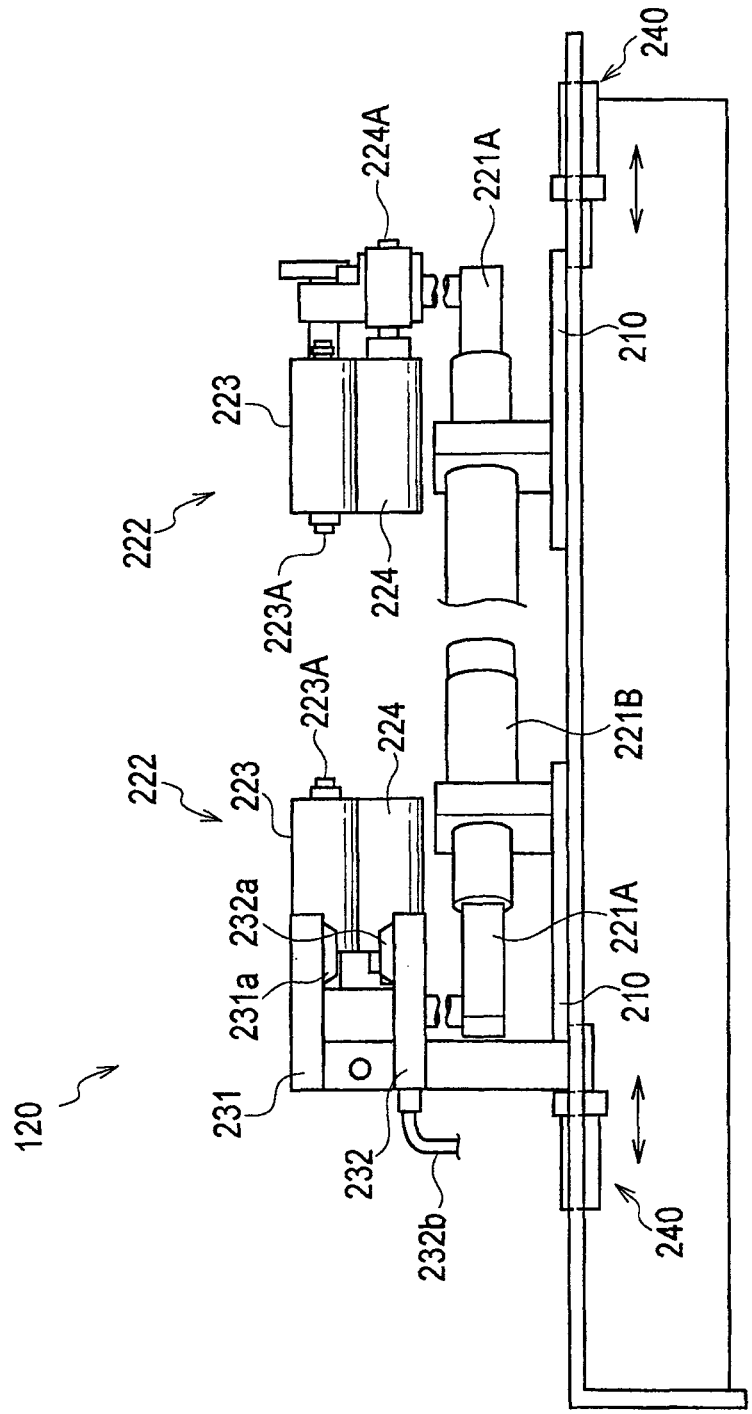
FIG. 4 is a front view of the conveyor of FIG. 3.
Figure 5:
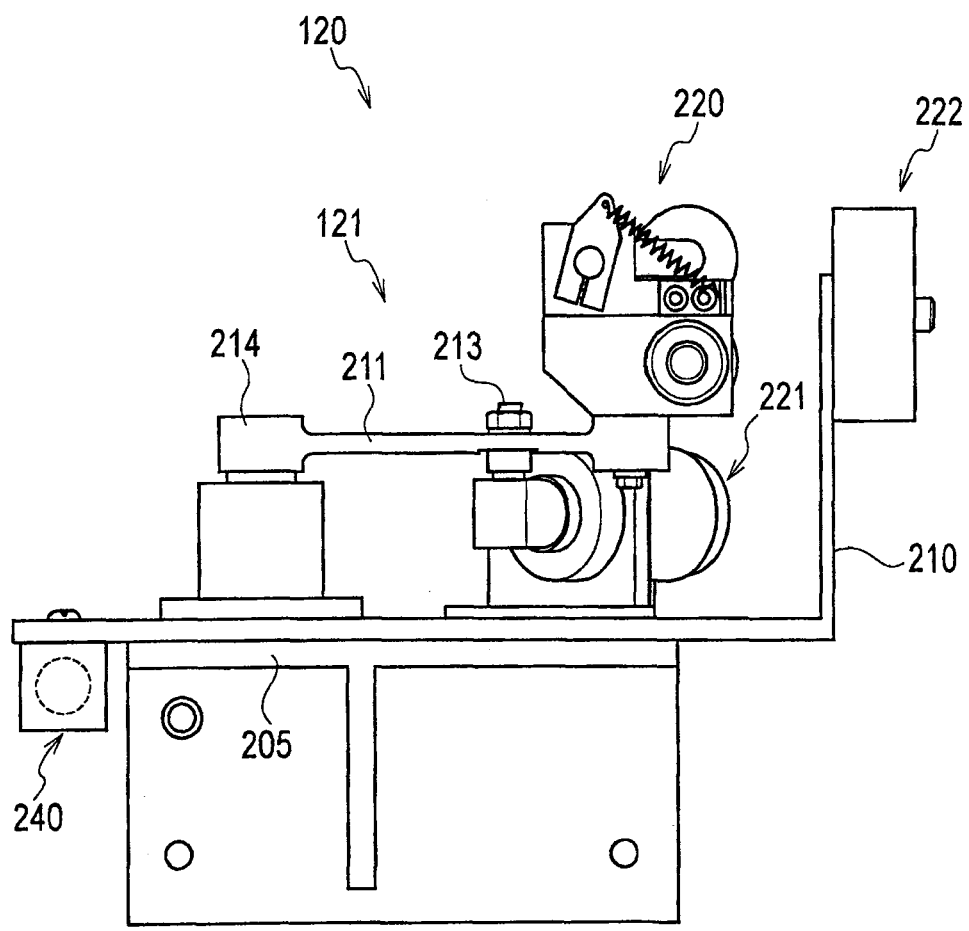
FIG. 5 is a side view of the conveyor of FIG. 3.

Hereinafter, a configuration of the conveyor 100 used in the conveying step and the changing step will be described with reference to FIGS. 3-5. FIG. 3 is a plan view of the conveyor 100 according to one or more embodiments. FIG. 4 is a front view of the conveyor 100 as seen in the direction of arrow A in FIG. 3. FIG. 5 is a side view of the conveyor 100 as seen in the direction of arrow B in FIG. 3.

Since the conveyors 100 used in the conveying steps before the steps (S1 to S6) have the same configuration, the description will be provided by taking, as an example, the conveyor 100 that conveys the web 7 before the waistline forming step S1.

As shown in FIGS. 3 to 5, the conveyor 100 conveys the web 7 under tension in the conveyance direction MD of the web 7. The conveyor 100 can convey webs 7 of different sizes (i.e., widths) such as a web 7L for L size or a web 7M for M size. In FIG. 3, the conveyor 100 is illustrated as conveying the web 7L for L size. The conveyor 100 includes a conveyor mechanism 110 and a side edge adjusting mechanism 120.

The conveyor mechanism 110 includes multiple rollers 111 configured to rotate along with conveyance of the web 7. At least one roller 111 of the multiple rollers 111 is driven to rotate about a shaft 111A by a drive unit (unillustrated). The drive unit includes a motor, or the like, configured to rotate the roller 111 through the shaft 111A.

The side edge adjusting mechanism 120 changes the passing position (FIG. 3 position Pr1, Pr2) of a side edge portion (the first side edge portion 10A or the second side edge portion 20A) of the web 7 being conveyed by the conveyor mechanism 110. The side edge adjusting mechanism 120 includes a first adjusting mechanism 121 and a second adjusting mechanism 122. The first adjusting mechanism 121 is configured to change the passing position (FIG. 3 position Pr1) of the first side edge portion 10A of the web 7 during conveyance, and the second adjusting mechanism 122 is configured to change the passing position (FIG. 3 position Pr2) of the second side edge portion 20A of the web 7 during conveyance.

The first adjusting mechanism 121 and the second adjusting mechanism 122 are attached to a base plate 205 across which the web 7 travels. The first adjusting mechanism 121 and the second adjusting mechanism 122 operate independently of each other, but practically have the same configuration. For this reason, only the configuration of the first adjusting mechanism 121 will be mainly described below. In the drawings, the same reference numerals denote the same elements or portions in the first adjusting mechanism 121 and the second adjusting mechanism 122.

The first adjusting mechanism 121 includes a movable plate 210, a guide mechanism 220, a detection mechanism 230 and a drive mechanism 240. The movable plate 210 is attached to the base plate 205 so as to be movable in the cross direction CD of the web 7.

The guide mechanism 220 is attached to the movable plate 210. The guide mechanism 220 changes the passing position of the first side edge portion 10A of the web 7. Specifically, the guide mechanism 220 includes an actuator 221 and a roller unit 222.

In the plan view of the web 7 (see FIG. 3), the actuator 221 rotates an upper nip roller 223 and a lower nip roller 224, which will be described later, about one end of a shaft 223A of the upper nip roller 223 and one end of a shaft 224A of the lower nip roller 224, respectively. The actuator 221 includes a slide arm 221A, a servomotor 221B configured to extend and contract the slide arm 221A, and a ball screw joint unit (unillustrated) interposed between the servomotor 221B and the slide arm 221A.

An end portion of the slide arm 221A is connected to an end portion 212 of a swing arm 211 with a connecting shaft 213. The swing arm 211 is attached to the movable plate 210, more specifically, is rotatably attached to the movable plate 210 with a fixed shaft 214.

The roller unit 222 is attached to the end portion 212 of the swing arm 211. The roller unit 222 includes the upper nip roller 223 and the lower nip roller 224. The upper nip roller 223 rotates about the shaft 223A, and comes into contact with one of the surfaces (upper surface) of the web 7. The lower nip roller 224 rotates about the shaft 224A and comes into contact with the other surface (lower surface) of the web 7. In other words, the lower nip roller 224 faces the upper nip roller 223 across the web 7.

The detection mechanism 230 is provided downstream of the guide mechanism 220 in the conveyance direction MD of the web 7. The detection mechanism 230 is electrically connected to the actuator 221, and detects the passing position of the first side edge portion 10A of the web 7. The detection mechanism 230 compares the detected passing position of the first side edge portion 10A of the web 7 (FIG. 3 position Pr1) with a predetermined position where the first side edge portion 10A of the web 7 (FIG. 3 position Pp1) is supposed to pass in the manufacturing process of the absorbent article 1. The detection mechanism 230 calculates a direction and a distance which are necessary to move the first side edge portion 10A to the predetermined position.

The detection mechanism 230 includes a projector 231a mounted on an upper arm 231, and a photodetector 232a provided below the projector 231a across the web 7 and mounted on a lower arm 232. The photodetector 232a is connected to the actuator 221 through an output cord 232b. The detection mechanism 230 detects the light emitted from the upper projector 231a using the photodetector 232a. Specifically, the detection mechanism 230 detects the position of the web 7 based on the amount of light detected by the photodetector 232a. Incidentally, the projector 231a may be mounted on the lower arm 232. Further, the photodetector 232a may be mounted on the upper arm 231. In FIG. 4, the detection mechanism 230 of the second adjusting mechanism 122 is omitted.

Here the guide mechanism 220 and the detection mechanism 230 are coupled to each other by the movable plate 210. In other words, the guide mechanism 220 and the detection mechanism 230 are moved together in the cross direction CD of the web 7 by the drive mechanism 240 as disclosed herein. Here, this together movement includes a movement in which the guide mechanism 220 and the detection mechanism 230 move together, and also a movement in which the guide mechanism 220 and the detection mechanism 230 move together while changing the passing position of the side edge portion of the web 7.

The drive mechanism 240 moves the movable plate 210 thereby to move the guide mechanism 220 and the detection mechanism 230 together in the cross direction CD of the web 7 according to a size of the web 7, such as L size or M size. More specifically, the drive mechanism 240 moves the guide mechanism 220 and the detection mechanism 230 together by moving the movable plate 210 in the cross direction CD of the web 7 according to a width $W_L$ of the web 7 for L size, or a width $W_M$ of the web 7 for M size.

Thus, the drive mechanism 240 moves the guide mechanism 220 and the detection mechanism 230 by the same traveling distance in the cross direction CD of the web 7. The drive mechanism 240 includes an actuator or the like electrically connected to the detection mechanism 230.

Hereinafter, an operation of the foregoing first adjusting mechanism 121 will be described with reference to FIGS. 3 to 5. Specifically, the following description will be provided for an operation of the first adjusting mechanism 121 in changing the size of the absorbent article 1 being manufactured.

As shown in FIGS. 3 to 5, the detection mechanism 230 compares the detected passing position of the first side edge portion 10A with a predetermined position for a predetermined size of the absorbent article 1. The drive mechanism 240 moves the guide mechanism 220 and the detection mechanism 230 in the cross direction CD of the web 7 according to the size such as L size or M size, that is, according to an instruction from the detection mechanism 230. Then, the guide mechanism 220 rotates the roller unit 222 by a certain angle by driving the actuator 221 according to the instruction from the detection mechanism 230.

In the case where the M size is changed to the L size, for example, the predetermined position is changed to correspond to the L size. In other words, the conveyor 100 is switched from the conveyance of the web 7M for M size to the conveyance of the web 7L for L size. For this switching, the drive mechanism 240 moves the guide mechanism 220 and the detection mechanism 230 outward in the cross direction CD of the web 7. Then, by rotating the roller unit 222 by a certain angle, the guide mechanism 220 can move, with an appropriate force, the edges 10A, 20A of the web 7 to the desired positions to increase or reduce the width $W_L$ or $W_M$ of the web 7.

As disclosed herein, the drive mechanism 240 moves the guide mechanism 220 and the detection mechanism 230 together in the cross direction CD of the web 7 (width direction) according to the size such as L size or M size, and also equalizes the traveling distances of the guide mechanism 220 and the detection mechanism 230 to each other in the cross direction CD of the web 7. In this case, the guide mechanism 220 (the actuator 221 and the roller unit 222) and the detection mechanism 230 are prevented from being misaligned in an inappropriate positional relationship, unlike the case where the guide mechanism 220 and the detection mechanism 230 are independently moved. Accordingly, even when the size of the absorbent article 1 to be manufactured is changed, the roller unit 222 is prevented from rotating by an erroneous amount, and no adjustment is needed to correct the positional relationship between the guide mechanism 220 and the detection mechanism 230 to the predetermined relationship. Thus, the passing positions of the first side edge portion 10A and the second side edge portion 20A of the web 7 can be changed without a need to perform complicated control.

As disclosed herein, the guide mechanism 220 and the detection mechanism 230 are coupled to each other by the single movable plate 210, and are moved in the cross direction CD of the web 7 by the drive mechanism 240. With this configuration, the guide mechanism 220 and the detection mechanism 230 are moved surely by the same travelling distance in the cross direction CD of the web 7. Thus, the guide mechanism 220 and the detection mechanism 230 are more surely prevented from being misaligned in an inappropriate positional relationship.

As disclosed herein, the guide mechanism 220 moves above the movable plate 210 in the cross direction CD of the web 7. With this configuration, the guide mechanism 220 is capable of fine adjustment in changes in the passing positions of the first side edge portion 10A and the second side edge portion 20A of the web 7. Therefore, the passing positions of the first side edge portion 10A and the second side edge portion 20A of the web 7 can be changed more easily.

MODIFIED EXAMPLES

The side edge adjusting mechanism 120 according to the foregoing description may be modified as follows. Here, the description will be provided mainly for the differences from the foregoing description, with the same or similar reference signs denoting the same or similar elements.

Modified Example 1

Figure 6:
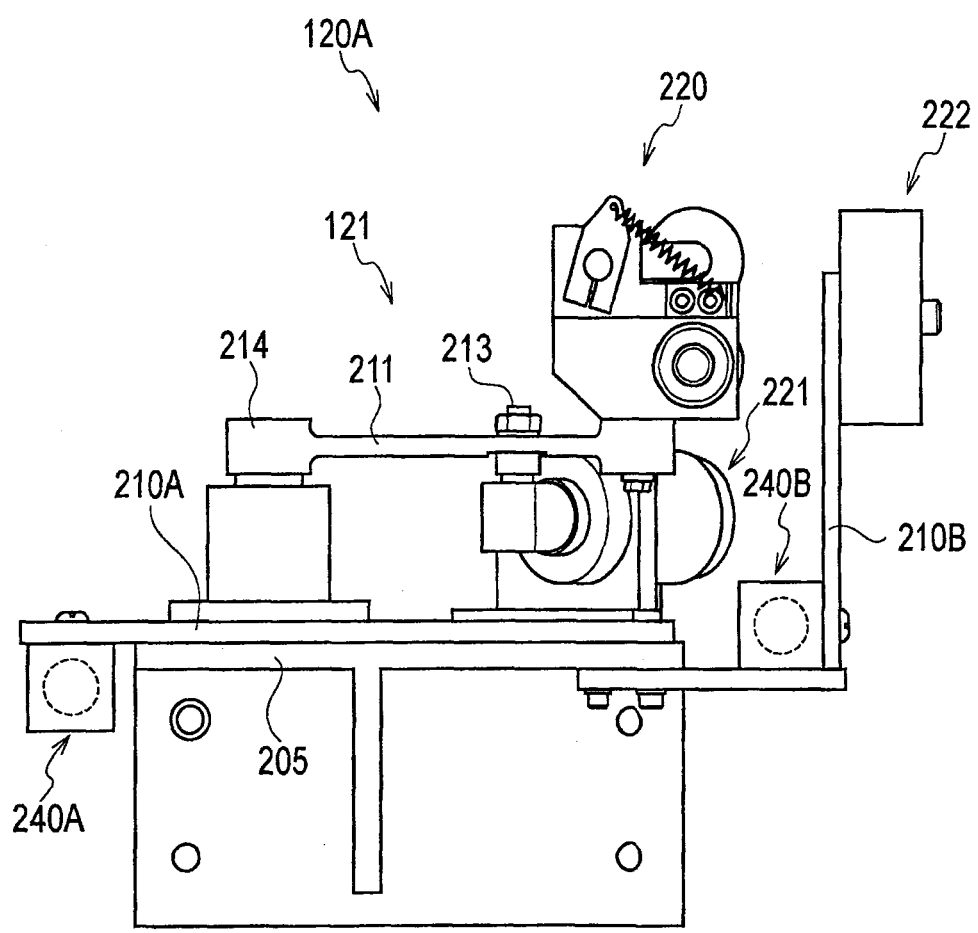
FIG. 6 is a side view of a side edge adjusting mechanism according to a Modified Example 1.

FIG. 6 is a side view of a side edge adjusting mechanism 120A according to a Modified Example 1. In the aforementioned description, the guide mechanism 220 and the detection mechanism 230 are coupled to the single movable plate 210. In contrast, in the Modified Example 1, a guide mechanism 220 and a detection mechanism 230 are independent of each other.

Specifically, as shown in FIG. 6, the guide mechanism 220 and the detection mechanism 230 are not coupled to each other by the movable plate 210. The guide mechanism 220 is coupled to a movable plate 210A, and is movable in the cross direction CD of the web 7 by a drive mechanism 240A. The detection mechanism 230 is coupled to a movable plate 210B, and is movable in the cross direction CD of the web 7 by a drive mechanism 240B.

The drive mechanisms 240A and 240B independently move the guide mechanism 220 and the detection mechanism 230, respectively, on the condition that the guide mechanism 220 and the detection mechanism 230 move by the same traveling distance in the cross direction CD of the web 7. Thus, the drive mechanisms 240A and 240B are capable of finely adjusting the guide mechanism 220 and the detection mechanism 230 independently, without misaligning the guide mechanism 220 and the detection mechanism 230 in an inappropriate positional relationship. Accordingly, the passing positions of the first side edge portion 10A and the second side edge portion 20A of the web 7 can be changed easily.

Modified Example 2

Figure 7:
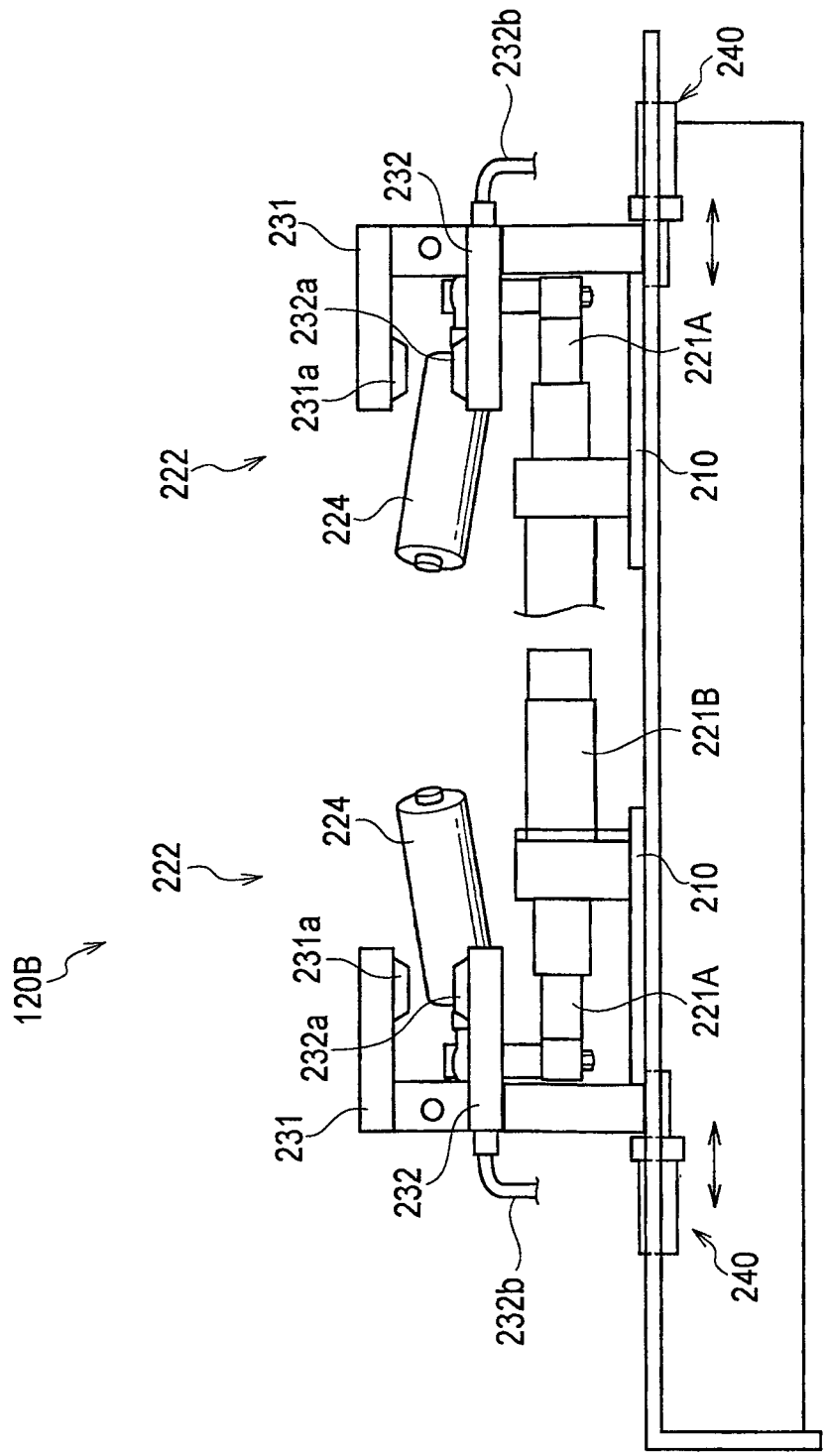
FIG. 7 is a front view of a side edge adjusting mechanism according to a Modified Example 2.

FIG. 7 is a front view of a side edge adjusting mechanism 120B according to a Modified Example 2. In the aforementioned description, the roller unit 222 includes the upper nip roller 223 and the lower nip roller 224. In contrast, in the Modified Example 2, a roller unit 222 includes only a lower nip roller 224.

Specifically, as shown in FIG. 7, the lower nip roller 224 is inclined to have a slope upward toward the web 7 in order to come into pressure contact with the web 7 from below. With this configuration, the lower nip roller 224 is capable of guiding the first side edge portion 10A of the web 7 to the predetermined position. The slope of the lower nip roller 224 can be adjusted to a degree appropriate according to properties, such as the flexibility, the stretchability, and the surface slipperiness, of the web 7.

The roller unit 222 does not necessarily include only the lower nip roller 224, but may include only an upper nip roller 223. In this case, the upper nip roller 223 is inclined to have a slope downward toward the web 7 in order to come into pressure contact with the web 7 from above.

In the Modified Example 2, having only any one of the upper nip roller 223 and the lower nip roller 224, the roller unit 222 is capable of obtaining the same advantageous effects as in the aforementioned description.

Modified Example 3

Figure 8:
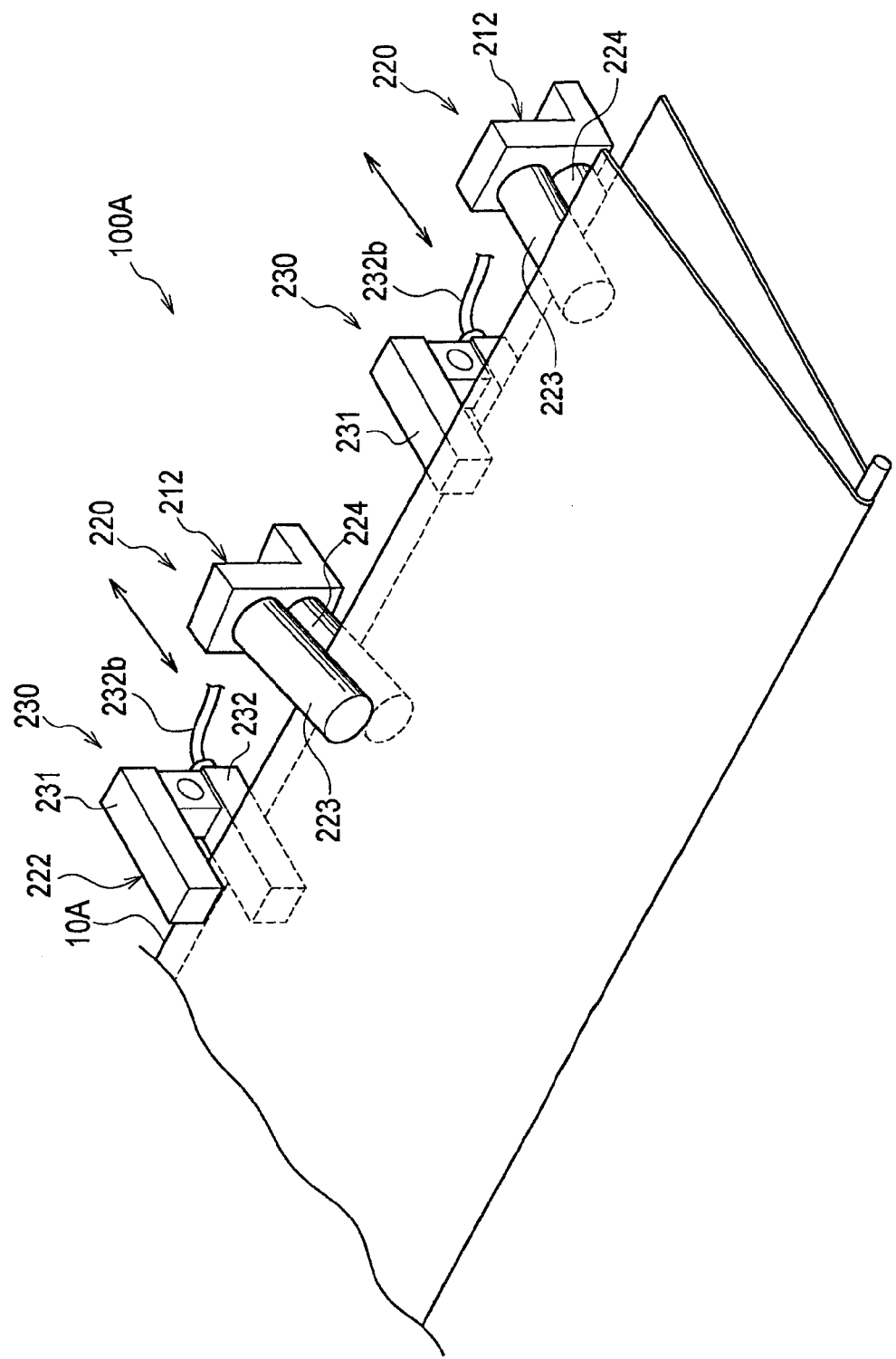
FIG. 8 is a perspective view of a conveyor according to a Modified Example 3.

FIG. 8 is a perspective view of a conveyor 100A according to a Modified Example 3. In the aforementioned description, the conveyor 100 is used between the steps (S1 to S6). In contrast, the conveyor 100 A in the Modified Example 3 is used in the folding step S4.

Specifically, as shown in FIG. 8, the conveyor 100A is provided in a location where the web 7 is folded along the folding line by bringing the first side edge portion 10A toward the second side edge portion 20A. To be more precise, an unillustrated movable plate 210, a guide mechanism 220, a detection mechanism 230 and an unillustrated drive mechanism 240 are provided to each of the first side edge portion 10A and the second side edge portion 20A.

In the Modified Example 3, in the folding step S4, the conveyor 100A is used and produces the same advantageous effects as in the aforementioned description even when the size of the absorbent article 1 is changed. As a result, the conveyor 100A allows the first side edge portion 10A to be surely placed exactly on the second side edge portion 20A in the web 7.

Further Embodiments

As described above, the details of several embodiments have been exemplarily disclosed. It should not be understood that the description and drawings which constitute part of this disclosure limit the present invention. Based on this disclosure, those skilled in the art may easily come up with various alternative embodiments, examples and operation techniques.

For example, the following additional embodiments can be envisaged. Specifically, the absorbent article 1 has been described as including, in combination, the front waistline portion 10, the back waistline portion 20 and the crotch portion 30. The absorbent article 1 is not limited to this configuration, but may be formed entirely as a single unit. In this case, needless to say, a different method of manufacturing such an absorbent article is employed.

Additionally, the description has been provided for the conveyor 100 used in the manufacturing of a pants-type disposal diaper. However, the conveyor 100 is not limited to such use. For example, the conveyor 100 may be used to manufacture another product such as an open-type disposal diaper, a sanitary napkin and a panty liner, for example. In other words, the conveyor 100 may be used at least for the conveyance of any web 7 that is stretchable in the cross direction CD of the web 7, not necessarily for the manufacturing of the absorbent article 1. As long as the conveyor 100 conveys a stretchable web 7, the conveyor 100 may be used between steps other than the steps described with respect to FIG. 2.

Moreover, the description has been provided for the conveyor 100 used to convey a single web 7. However, the conveyor 100 is not limited to such use. For example, when a web including a continuum of the front waistline portions 10 and a web including a continuum of the back waistline portions 20 are conveyed simultaneously, a single conveyor 100 may be provided for each or both of the webs. In addition, multiple conveyors 100 may be provided between any two of the process steps.

In addition, the absorbent article 1 has been described as having size variations such as L size and M size. The size variations are not limited to these sizes, but may include two or more different sizes. For example, the size variations may include three sizes such as L size, M size and S size.

Further, the conveyor mechanism 110 has been described as one including multiple rollers 111. However, the conveyor mechanism 110 should not be limited to this configuration, and may have another configuration, such as a belt conveyor, as long as the configuration allows the conveyor mechanism 110 to convey the web 7.

The side edge adjusting mechanism 120 has been described as one including the first adjusting mechanism 121 and the second adjusting mechanism 122. However, the side edge adjusting mechanism 120 should not be limited to this configuration, and may include only one of the adjusting mechanisms. In other words, the side edge adjusting mechanism 120 may be provided to at least one of the side edge portions of the web 7.

Additionally, although the movable plate 210 has been described as one coupling the guide mechanism 220 and the detection mechanism 230 to each other, a frame capable of coupling (fixing) the guide mechanism 220 and the detection mechanism 230 to each other may be used instead of the movable plate 210.

Further, there is no limitation to any positional relationship between the guide mechanism 220, the detection mechanism 230 and the drive mechanism 240, and thereby any appropriate positional relationship can be selected as desired.

Furthermore, a material, a condition of surface finishing, and the length and diameter of the nip rollers can be appropriately selected according to conditions of the web such as a processed condition of the web 7, and an adhesive-applied condition of an adhesive agent that is applied to the web 7 in advance. For example, materials usable as the surface material of the rollers include polyurethane rubber or silicone rubber, a sponge made of such rubber, and a metal.

As described above, the present invention naturally includes various embodiments which are not described herein. Accordingly, the technical scope of the present invention should be determined only by the matters to define the invention in the scope of claims regarded as appropriate based on the description.

The entire content of Japanese Patent Applications 2009-048418 (filed on Mar. 2, 2009) and 2010-042003(filed on Feb. 26, 2010) are incorporated herein by reference.

INDUSTRIAL APPLICABILITY

Therefore, since the conveyor and method of manufacturing absorbent article of the present invention provides is capable of selectively conveying any of webs for two or more sizes by easily changing a passing position of a side edge portion of the web without having to perform complicated control, it is useful in manufacturing technology for absorbent articles.

REFERENCE SIGNS LIST 1 absorbent article
2 top sheet
3 back sheet
4 absorber
5 waterproof sheet
6 gather
6A waist gather
6B leg gather
7, 7A, 7B, 7L, 7M web
10 front waistline portion
10A first side edge
20 back waistline portion
20A second side edge
30 crotch portion
30A crotch portion member
40 leg-surrounding openings
50 joint portions
50A joint region
60 waist openings
100, 100A conveyor
110 conveyor mechanism
111 roller
111A shaft core
120 (120A, 120B) side edge adjusting mechanism
121 first adjusting mechanism
122 second adjusting mechanism
205 base plate
210 movable plate
220 guide mechanism 221 actuator
222 roller unit
223 upper nip roller
224 lower nip roller
230 detection mechanism
231 upper arm
231a upper projector
232 lower arm
232a lower projector
232b output cord
240 (240A, 240B) drive mechanism

The invention claimed is:

1. A conveyor for selectively conveying one of a continuous web having a first size and a continuous web having a second size different from the first size, said conveyor comprising:
 a guide mechanism configured to change a passing position of at least one of first and second side edge portions of the web by being in contact with the at least one side edge portion of the web;
 a detection mechanism configured to detect the passing position of the side edge portion of the web; and
 a drive mechanism configured to move the guide mechanism and the detection mechanism by an equal traveling distance in a cross direction perpendicular to a conveyance direction of the web according to the first size or the second size of the web being conveyed.

2. The conveyor according to claim 1, wherein the drive mechanism is configured to move the guide mechanism and the detection mechanism together in the cross direction.

3. The conveyor according to claim 1, wherein
 the guide mechanism and the detection mechanism are coupled to a single frame that is moveable by the drive mechanism in the cross direction of the web.

4. The conveyor according to claim 3, wherein the guide mechanism is movable on the frame in the cross direction of the web.

5. The conveyor according to claim 1, wherein the guide mechanism includes
 a nip roller unit including a shaft core and configured to be in contact with the side edge portion of the web, and
 an actuator configured to rotate the shaft core of the nip roller unit about one end of the shaft core of the nip roller unit in a plan view of the web.

6. The conveyor according to claim 5, wherein the nip roller unit includes
 a first nip roller configured to be in contact with one of surfaces of the web, and
 a second nip roller facing the first nip roller across the web and configured to be in contact with the other surface of the web.

7. The conveyor according to claim 1, wherein
 the guide mechanism defines a first guide mechanism and the conveyor further comprises a second guide mechanism, and
 the first guide mechanism and the second guide mechanism are configured to operate independently with each other.

8. The conveyor according to claim 7, wherein the first guide mechanism is configured to change the passing position of the first side edge portion of the web by being in contact with the first side edge portion of the web, and
 the second guide mechanism is configured to change the passing position of the second side edge portion of the web by being in contact with the second side edge portion of the web.

9. The conveyor according to claim 2, wherein the guide mechanism and the detection mechanism are configured to move together in the cross direction while changing the passing position of said at least one side edge portion of the web.

10. The conveyor according to claim 7, wherein the first guide mechanism is configured to be located at the first side edge portion of the web, and the second guide mechanism is configured to be located at the second side edge portion of the web.

11. The conveyor according to claim 10, wherein the detection mechanism defines a first detection mechanism configured to move together with the first guide mechanism, and the conveyor further comprises a second detection mechanism configured to move together with the second guide mechanism.

12. The conveyor according to claim 11, further comprising first and second movable frames coupled to the first and second guide mechanisms and coupled to the first and second detection mechanisms correspondingly,
 wherein the first guide mechanism is moveable independently from the second guide mechanism, and
 wherein the first detection mechanism is moveable independently from the second detection mechanism.

13. The conveyor according to claim 1, wherein the guide mechanism is configured to bring the first side edge portion of the web toward the second side edge portion of the web for folding the web and to adjust a position of the first side edge portion to coincide with the second side edge portion of the folded web.

* * * * *